United States Patent
Gregorio et al.

(10) Patent No.: US 7,086,859 B2
(45) Date of Patent: Aug. 8, 2006

(54) COMPACT DIGITAL INTRAORAL CAMERA SYSTEM

(75) Inventors: John Joseph Gregorio, Chana, IL (US); Steven R. Jambor, Chicago, IL (US); David Harvey Cooper, Carlsbad, CA (US)

(73) Assignee: Gendex Corporation, Washington, DC (US)

( * ) Notice: Subject to any disclaimer, the term of this patent is extended or adjusted under 35 U.S.C. 154(b) by 218 days.

(21) Appl. No.: 10/458,417

(22) Filed: Jun. 10, 2003

(65) Prior Publication Data

US 2004/0253563 A1   Dec. 16, 2004

(51) Int. Cl.
   *A61C 1/00*   (2006.01)
(52) U.S. Cl. .............................. 433/29; 348/376
(58) Field of Classification Search ............. 433/29; 348/373, 375, 376, 552; 600/101, 109, 112, 600/118, 178

See application file for complete search history.

(56) References Cited

U.S. PATENT DOCUMENTS

| | | | |
|---|---|---|---|
| 4,259,582 A | 3/1981 | Albert | 250/402 |
| 4,418,419 A | 11/1983 | Schreiber et al. | 378/40 |
| 4,589,121 A | 5/1986 | Makino | 378/39 |
| 4,628,356 A | 12/1986 | Spillman et al. | 358/111 |
| 4,694,478 A | 9/1987 | Delnon | 378/39 |
| 4,782,503 A | 11/1988 | Molitor et al. | 378/169 |
| 4,783,793 A | 11/1988 | Virta et al. | 378/39 |
| 4,831,645 A | 5/1989 | Guenther et al. | 378/205 |
| 4,852,134 A | 7/1989 | Kinanen et al. | 378/38 |
| 4,856,038 A | 8/1989 | Guenther et al. | 378/39 |
| 4,907,251 A | 3/1990 | Mork et al. | 378/39 |
| 4,985,907 A | 1/1991 | Moteni | 378/139 |
| 5,018,177 A | 5/1991 | McDavid et al. | 378/62 |
| 5,027,138 A * | 6/1991 | Gandrud | 348/66 |
| 5,179,579 A | 1/1993 | Dove et al. | 378/38 |
| 5,195,114 A | 3/1993 | Sairenji et al. | 378/40 |
| 5,214,686 A | 5/1993 | Webber | 378/38 |
| 5,293,312 A | 3/1994 | Waggener | 364/413.21 |
| 5,343,391 A | 8/1994 | Mushabac | 364/413.28 |
| 5,429,502 A * | 7/1995 | Cooper et al. | 433/29 |
| 5,539,799 A | 7/1996 | Schulze-Ganzlin et al. | 378/207 |
| 5,579,361 A | 11/1996 | Augais et al. | 378/38 |
| 5,589,874 A * | 12/1996 | Buchin | 348/72 |
| 5,590,167 A | 12/1996 | Arai | 378/38 |
| 5,600,699 A | 2/1997 | Suzuki et al. | 378/38 |
| 5,640,018 A | 6/1997 | Suzuki et al. | 250/368 |
| 5,664,001 A | 9/1997 | Tachibana et al. | 378/98.8 |
| 5,702,249 A * | 12/1997 | Cooper | 433/29 |
| 5,737,013 A * | 4/1998 | Williams et al. | 348/66 |
| 5,743,731 A * | 4/1998 | Lares et al. | 433/29 |
| 5,744,806 A | 4/1998 | Fröjd | 250/370.09 |
| 5,784,429 A | 7/1998 | Arai | 378/38 |
| 5,793,838 A | 8/1998 | Kovacs | 378/39 |
| 5,812,191 A | 9/1998 | Orava et al. | 348/308 |
| 5,848,123 A | 12/1998 | Strömmer | 378/98.8 |
| 5,872,364 A | 2/1999 | Strömmer | 250/370.09 |
| 5,997,176 A | 12/1999 | Fairleigh | 378/196 |
| 6,018,563 A | 1/2000 | Arai et al. | 378/39 |

(Continued)

FOREIGN PATENT DOCUMENTS

EP    0 673 623    9/1995

(Continued)

*Primary Examiner*—Cary E. O'Connor
*Assistant Examiner*—Patrick J. Kilkenny
(74) *Attorney, Agent, or Firm*—McNees Wallace & Nurick LLC

(57) ABSTRACT

The present invention is a true digital output intraoral camera with a docking station.

20 Claims, 3 Drawing Sheets

U.S. PATENT DOCUMENTS

| | | | |
|---|---|---|---|
| 6,019,721 A * | 2/2000 | Holmes et al. | 600/167 |
| 6,035,013 A | 3/2000 | Orava et al. | 378/37 |
| 6,081,739 A | 6/2000 | Lemchen | 600/407 |
| 6,097,902 A | 8/2000 | Blumé | 396/569 |
| 6,118,842 A | 9/2000 | Arai et al. | 378/39 |
| 6,132,211 A * | 10/2000 | Peithman | 433/29 |
| 6,152,731 A | 11/2000 | Jordan et al. | 433/69 |
| 6,169,780 B1 | 1/2001 | Yoshimura et al. | 378/39 |
| 6,173,035 B1 | 1/2001 | Tachibana et al. | 378/39 |
| 6,196,715 B1 | 3/2001 | Nambu et al. | 378/197 |
| 6,219,401 B1 | 4/2001 | Tachibana et al. | 378/39 |
| 6,220,751 B1 | 4/2001 | DiGiacomo et al. | 378/182 |
| 6,230,934 B1 | 5/2001 | Kramer | 378/98.8 |
| 6,276,934 B1 * | 8/2001 | Rakocz | 433/29 |
| 6,289,074 B1 | 9/2001 | Arai et al. | 378/4 |
| 6,358,047 B1 * | 3/2002 | Lehmann | 433/26 |
| 6,398,549 B1 * | 6/2002 | Koivisto et al. | 433/29 |
| 6,404,854 B1 | 6/2002 | Carroll et al. | 378/98.8 |
| D468,429 S * | 1/2003 | Bareth et al. | D24/152 |
| 6,563,532 B1 * | 5/2003 | Strub et al. | 348/158 |
| 6,573,938 B1 * | 6/2003 | Schulz et al. | 348/373 |
| 6,761,561 B1 * | 7/2004 | Mandelkern et al. | 433/29 |
| 2001/0055368 A1 | 12/2001 | Carroll | 378/189 |
| 2002/0051216 A1* | 5/2002 | Hudson et al. | 358/302 |
| 2002/0064751 A1* | 5/2002 | Lehmann | 433/26 |
| 2002/0067407 A1 | 6/2002 | Cooper | 348/66 |
| 2003/0025789 A1* | 2/2003 | Saito et al. | 348/76 |

FOREIGN PATENT DOCUMENTS

| | | |
|---|---|---|
| EP | 0 608 237 | 10/1996 |
| EP | 0 776 124 | 5/1997 |
| EP | 0 776 126 | 5/1997 |
| EP | 0 853 427 | 7/1998 |
| EP | 0 854 639 | 7/1998 |
| EP | 0 854 643 | 7/1998 |
| EP | 0 854 644 | 7/1998 |
| EP | 0 904 734 | 3/1999 |
| EP | 1 132 755 | 9/2001 |
| WO | 95/33332 | 12/1995 |
| WO | 02/082820 | 10/2002 |

* cited by examiner

COMPACT DIGITAL INTRAORAL CAMERA SYSTEM

TECHNICAL FIELD

The present invention is a true digital output intraoral camera with a compact docking station.

BACKGROUND OF THE INVENTION

Intraoral cameras such as The AcuCam Concept III from DENTSPLY International Inc., are known to be useful in the art. Real time images of the oral cavity can be displayed for purposes of diagnosis, treatment, patient education and the like.

It will be appreciated that the dental professional has a wide range of useful equipment with which patient treatments can be effected. While this results in improved patient care, the professional must be cognizant of the physical space requirements of equipment and the office within which it is used.

A need exists therefore, for smaller and improved equipment. According to the present invention, a camera system provides digital video output and has the ability to integrate into existing dental office furniture such as the dental chair/unit or the cabinetry in a space-saving manner.

BRIEF DESCRIPTION OF THE DRAWING

Whenever possible, the same reference numbers will be used throughout the drawings to refer to the same or like parts.

PREFERRED EMBODIMENT FOR CARRYING OUT THE INVENTION

Figure 4:
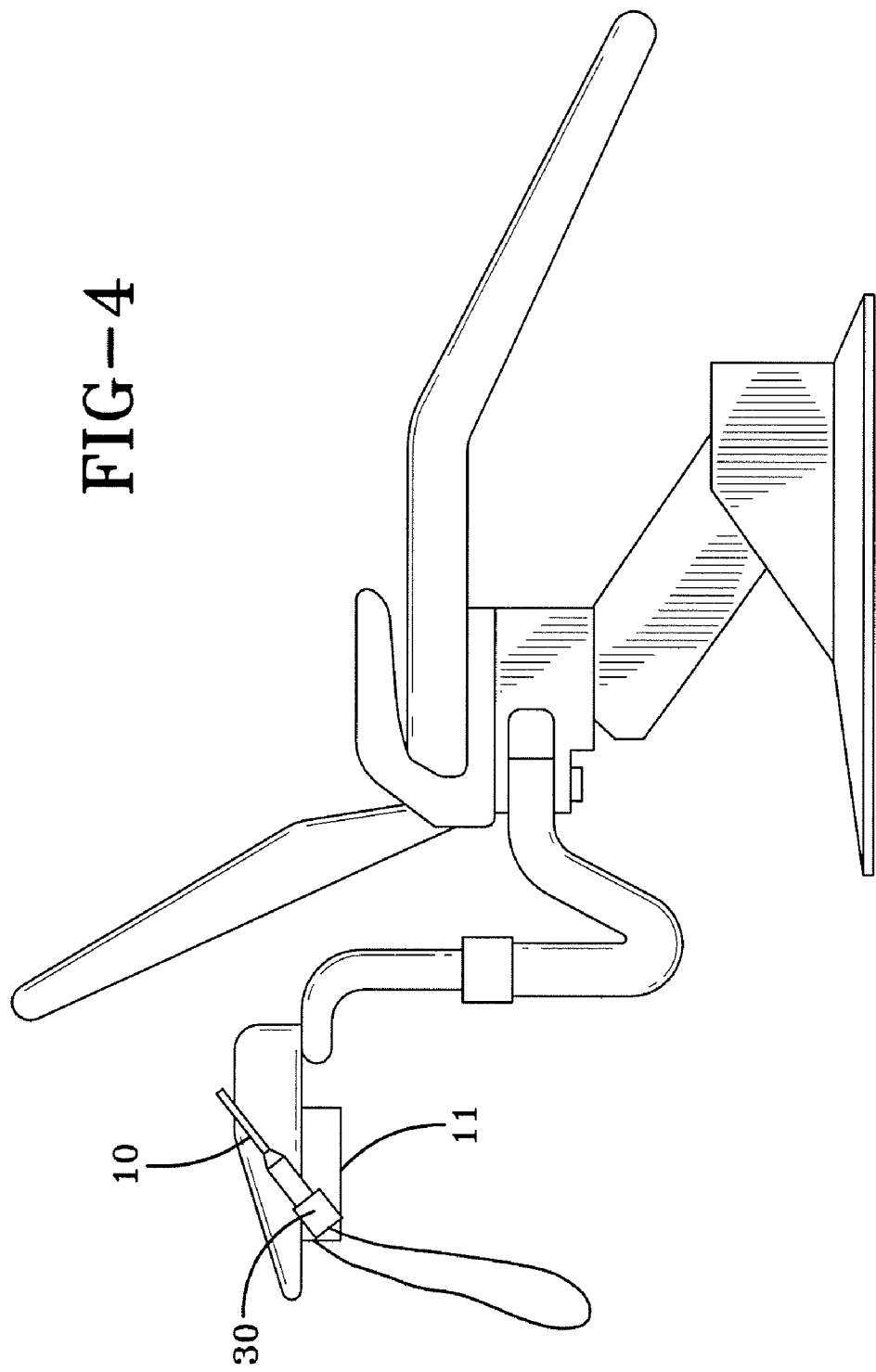
FIG. 4 shows the camera system of the present invention mounted on a delivery system for a dental chair.

The present invention provides an intraoral camera 10 having a docking station 11 that is miniaturized in order to fit into smaller spaces in the dental operatory. The docking station 11 is preferably designed to fit under the delivery unit of a conventional dental chair as shown in FIG. 4. With the present invention, a dedicated footswitch is no longer necessary because images will be saved via the computer. However, the new docking station 11 may have the connection and electronics to connect a conventional footswitch. According to the invention, control commands are transferred via a Firewire connection 12.

This product is a dental intraoral camera 10 with direct digital video output via Firewire 12 connection and protocol (IEEE 1394 standard). It employs a conventional intraoral camera handpiece 10, such as DENTSPLY's AcuCam Concept IV handpiece camera, or a variation thereof, with the new docking station 11. The docking station 11 is more compact than in the station's heretofore known in the art, and can be integrated with a dental unit (chair) or in a dental cabinet. The docking station 11 is preferably powered by a low-voltage external supply. It includes the electronics necessary to convert the handpiece S-Video to a Firewire digital output. This output interfaces to any Firewire equipped computer that complies with the IEEE 1394A standard.

As an example, a digital intraoral camera system having a compact footprint according to the invention, has the following general characteristics.

Compact footprint approximately 150×150×50 mm, or smaller.

Single S-Video input via a Lemo type 10-pin connector with fiberoptic ferrule.

Provides standard S-Video and uncompressed Firewire outputs.

The power supply physical size does not exceed approximately 100×100×50 and preferably has two cables one to the AC input and the other end to the Docking station.

Input power range from 90 to 265V, 50–60 Hz.

Provides an IEEE1394A Firewire output to interface to a standard Windows Computer using Windows OS via a 3–4.5 Meters Firewire cable.

Provides S-Video output to external devices.

A switch to turn off the lamp and blank the video signal when the handpiece is holstered.

Ergonomic docking station designed for dental chair mounting, wall mounting, counter top placement, or flush mounting in a cabinet.

Size/shape compatible with most popular chair systems, e.g. Adec, or Royal and for mounting below a delivery system.

Footswitch connection for routing to a computer.

The chassis is preferably formed from 1-mm thick, zinc plated steel, with ventilation slots to provide the necessary forced air cooling of critical components. The ventilation slots conform to the IEC-60601-1 requirements to prevent a standard probe from reaching electrical components. The Docking Station provides a holster to hold the handpiece, which may be attached to the chassis, or located remotely. The holster will have a built-in light sensor to implement automatic lamp and camera activation when the instrument is removed from the holster. The chassis top cover snaps into slots in the chassis sides and provides an EMC environment. Brackets will be provided to enable flush mounting in cabinets.

The top cover 20 or bezel is preferably molded from UV stabilized Lexan, or equivalent material. The material should conform to UL-2601, FDA and IEC-60601-1 requirements. The top cover is applied in counter-top, chair-mount and wall-mount applications. The bezel is used when the Docking Station is flush mount in cabinet space. The top cover and bezel are designed to be aesthetically and ergonomically pleasing, with clean modern lines and suitable for a medical environment. They will be essentially smooth to permit easy cleaning, and free of ridges, or fluting, which could form a bacteria trap and will mate aesthetically and cleanly with a molded front connector panel, which will support the Lemo type receptacle and provide the necessary isolation.

Figure 1:
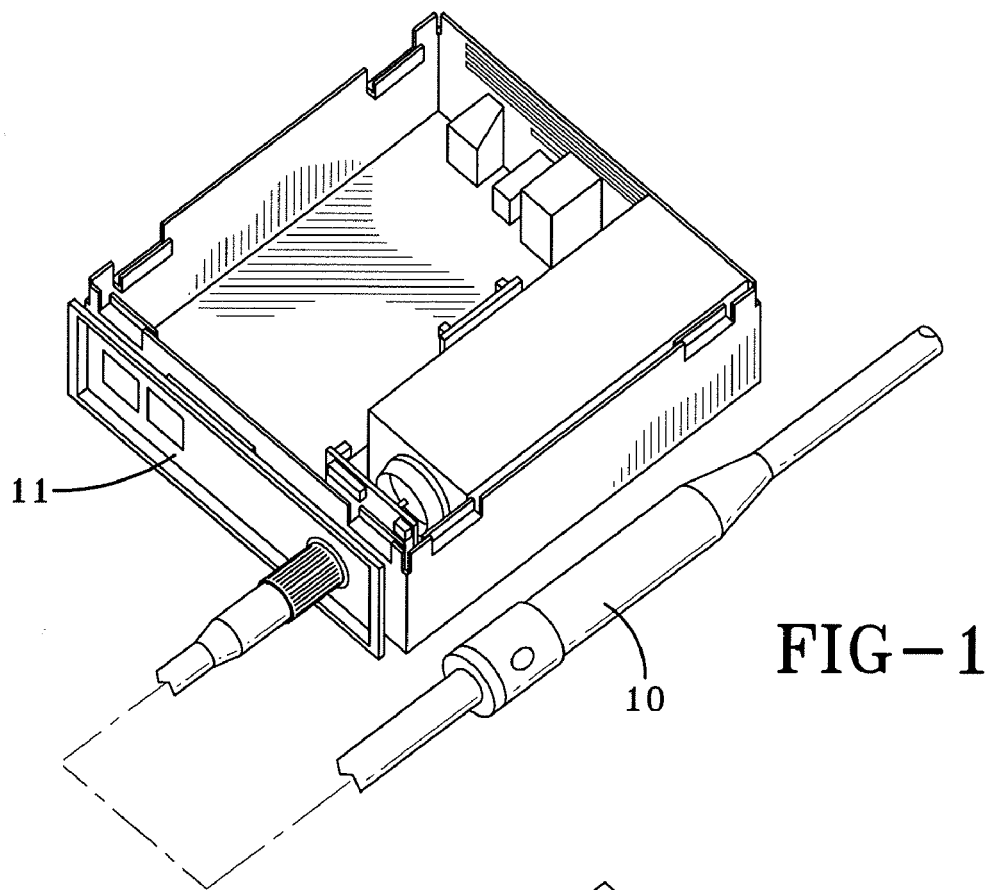
FIG. 1 shows an intraoral camera system according to the concepts of the present invention.
Figure 2:
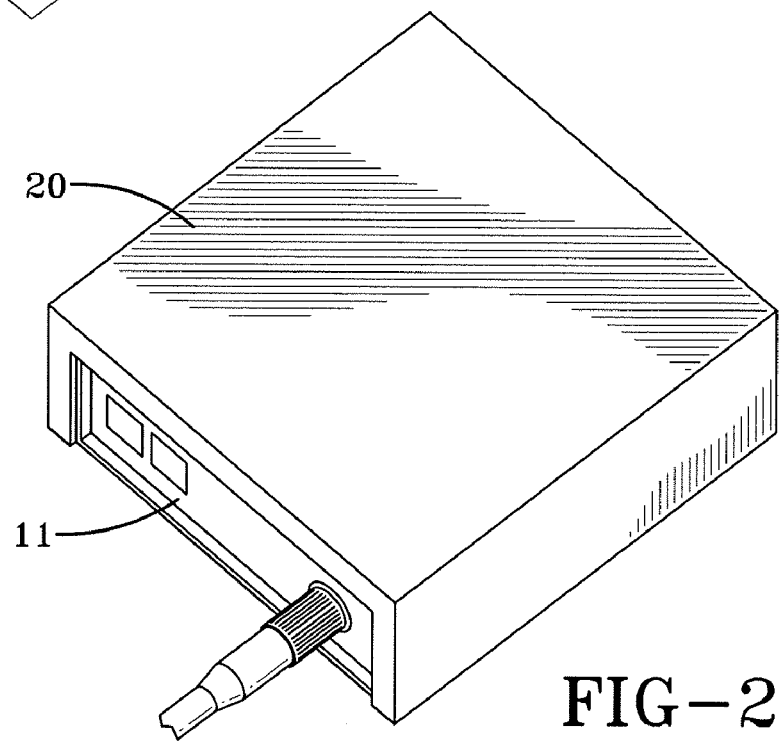
FIG. 2 shows the docking station of the system of FIG. 1 with a cover in place.
Figure 3:
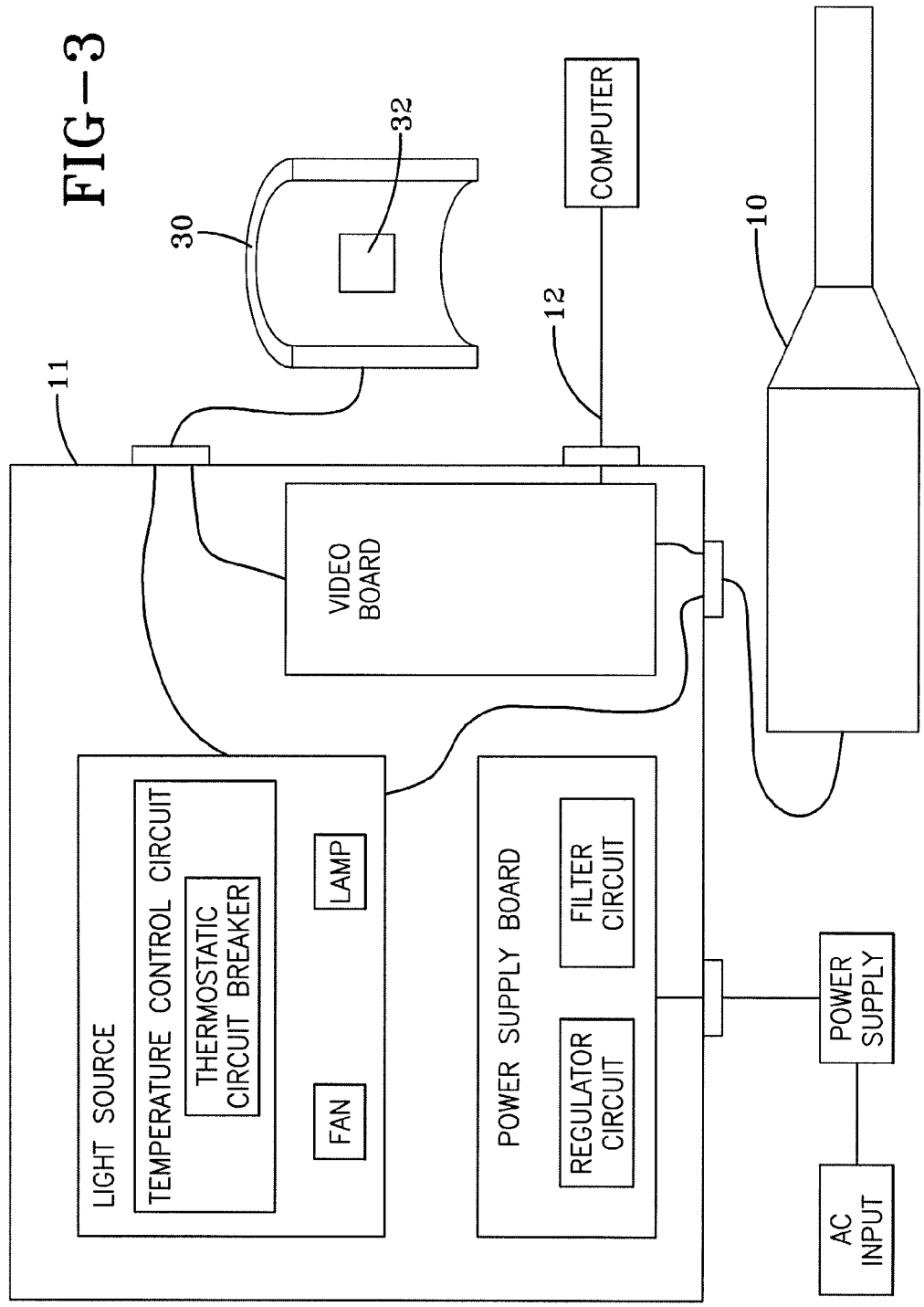
FIG. 3 shows schematically the arrangement of components of the camera system of the present invention.

As shown in FIG. 3, the docking station components include a light source assembly; a Firewire/video board with patient connected circuit isolation; a power supply board with regulator and filter circuits that may be combined with the Firewire/video board; a single, low noise 12 VDC fan with ball bearings; a 12 VDC input connector; Firewire, S-Video and footswitch output connectors; Lemo type receptacle connector board as conventionally used in the Concept IV docking station; a top cover; substantially total EMI shielding; and a 12 VDC external power supply.

The present system uses a docking station having a light source, such as a conventional source. For example, one usefull light source is that used with the Concept IV docking station, which has a 2,000 hour, 12 volt, 75 W-halogen lamp, with a modified mount. The focusing system consists of a spherical reflector and a pair of aspherical focusing elements. All optical elements are mounted in such a way to avoid differential expansion problems.

The light source assembly is preferably mounted in an aluminum tube with an ID of approximately 25 mm. The tube is cooled by a low noise, 12 VDC fan and is provided with a thermostatic circuit breaker to cut off the lamp current if the temperature rises above 167 F in event of fan failure. The light source chassis mount is designed to force the entire flow of air through the fan to pass over the tube. Easy access is provided for lamp replacement by removing the top cover. The fan is powered from the 12 VDC power input via suitable EMI filter components.

Referring back to FIG. 3, the docking station preferably includes a holster 30 to support the camera head and cable when not in use. The lamp is turned off and the video signal is blanked when the camera 10 is in the holster 30. The holster 30 can either be mounted on the chassis, or remotely. Preferably, the holster 30 includes a switch 32 with a passive means to sense the presence of the handpiece 10, such as a magnet interacting with hall effect, or magneto-resistive element in the handpiece 10, or the like. Alternatively, a version of the switch 32 within the scope of the invention utilizes a sensor assembly (Led/photo-transistor set) to detect the presence of the camera in the holster 30. The preferred modification provides a miniature 4-pin connector located in the hollow compartment of an otherwise conventional holster 30, such as that found in the Concept IV holster. This connects directly to the sensor assembly when the holster 30 is chassis mounted, or via an extension cable in remote applications.

In the case of the magnetic holsters, the handpiece sensor will be connected through the camera cable to the Firewire/Video board via an optical isolator. This would utilize the ATW wire, if available in the new HRDSP design. In the case of the conventional and modified Concept IV holster, the sensor will be connected by a harness to the Firewire/Video board.

General functional performance characteristics of the present invention include:

The Firewire will provide 4.2.2 video to a computer.

Handpiece S-Video input, Firewire output with no compression, (DCAM standard).

Full performance, 480 TV lines (support) NTSC, or 525 TV lines PAL formats.

Provides footswitch control, which information is then passed to (the software in) the computer.

Analog S-Video output connector interfacing to an S-Video peripherals. Supports isochronous transfers.

General operation of the hardware interface includes the following:

The system provides S-video isolation via video optical isolators. Then the S-video signal is converted from analog S-video to 4:2:2 digital data and sent to the link layer controller chip.

The data is converted into packets which serializes the video signal data and sends them to the Physical Layer output chip.

The Microprocessor will program the Video decoder and the Firewire chips.

The CPLD does the address mapping and other I/O functions.

The CPLD can be programmed via a JTAG port and the Microprocessor can be programmed via the RS232 port.

$I^2C$ support to control the handpiece programming.

Sensing of the removal of the handpiece.

1500V isolation of the patient connected circuits, including the S-Video input, the circuit to sense if the handpiece is plugged into the docking station, and whether the handpiece is holstered, if a magnetic sensor is used.

A Firewire chip set to provide an uncompressed isochronous Firewire video output.

A footswitch input through which commands can be routed to the computer through the Firewire interconnects.

All I/O signal and commands to be EMI filtered as required.

General operation characteristics of the software interface include the following:

Supports 30 frames per second update rate at full resolution;

Single frame capture image storage;

Real-time capture;

Supports image stabilization;

Supports footswitch control.

The present camera system preferably provides single fault protection, and is compliant with the CE mark requirements and the safety requirements of IEC-60601-1, UL2601 and CSA.

It will be appreciated therefore, that a digital intraoral camera according to the present invention provides an improvement in the intraoral camera art, and is otherwise a useful and valuable contribution to the state of that art.

What is claimed is:

1. An intraoral digital camera system comprising:
    an intraoral digital camera operatively connected to a docking station;
    said docking station including:
        control circuitry to convert a video signal from said camera to a digital signal compatible with a digital output connection from said docking station; and
        a light source, said light source having a lamp and a temperature control circuit to prevent overheating of said light source; and
    a holster to support said camera, said holster including a switching arrangement configured to automatically control activation and deactivation of said light source and said camera.

2. The intraoral digital camera system of claim 1, wherein said video signal from said camera is S-Video.

3. The intraoral digital camera system of claim 1, wherein said digital output connection is compliant with the IEEE 1394 A Standard.

4. The intraoral digital camera system of claim 3, wherein said digital output connection provides a 4.2.2 video signal.

5. The intraoral digital camera system of claim 1, wherein said docking station is configured to be integrally mounted with an item of dental office furniture, and wherein said docking station has a footprint equal to or smaller than about 150 mm×150 mm×50 mm.

6. The intraoral digital camera system of claim 5, wherein said item of dental office furniture includes a dental chair.

7. The intraoral digital camera system of claim 6, wherein said docking station is configured to be mounted under a delivery unit of said dental chair.

8. The intraoral digital camera system of claim 1, wherein said temperature control circuit includes a thermostatic circuit breaker, said thermostatic circuit breaker being configured to prevent current to said lamp in response to a temperature associated with said light source exceeding a predetermined temperature level.

9. The intraoral digital camera system of claim 1, wherein said switching arrangement is configured to control activation of said lamp and start transmission of video signals from said camera in response to said camera being removed from said holster and said switching arrangement being configured to control deactivation of said lamp and stop transmission of video signals from said camera in response to said camera being placed in said holster.

10. The intraoral digital camera system of claim 9, wherein said switching arrangement comprises one of a magnetic sensing arrangement or a sensor assembly.

11. The intraoral digital camera system of claim 10, wherein said magnetic sensing arrangement comprises one of a magnet interacting with Hall Effect or a magneto-resistive element.

12. The intraoral digital camera system of claim 10, wherein said sensor assembly comprises a LED/phototransistor set.

13. The intraoral digital camera system of claim 1, wherein said docking station further includes a power supply board and a 12 VDC input connector.

14. The intraoral digital camera system of claim 1, further comprising a power supply, said power supply having a connection to an AC input and a connection to said docking station.

15. An intraoral digital camera system comprising:
 an intraoral digital camera;
 a docking station, the docking station being configured to be integrally mounted with an item of dental office furniture, the docking station including:
  an input connection to receive signals from the intraoral digital camera;
  a video board to convert the input signals from said camera to digital signals;
  at least one output connection to receive the digital signals from the video board;
  a power supply board, the power supply board having regulator and filter circuits; and
  a light source, said light source having a lamp, a fan, and a temperature control circuit to prevent overheating of said light source;
 a power supply, the power supply being external to the docking station and having a connection to an AC input and a connection to the docking station;
 a holster to support said camera, said holster including a switching arrangement configured to automatically control activation and deactivation of said light source and said camera.

16. The intraoral digital camera system of claim 15 wherein:
 the input connection is configured to receive S-Video signals from the camera;
 the at least one output connection is configured to receive IEEE 1394 A standard video signals from the video board; and
 the video board is configured to convert the S-Video signals from the camera to 4.2.2 digital data and convert the 4.2.2 digital data to IEEE 1394 A standard video signals for the at least one output connection.

17. The intraoral digital camera system of claim 15, wherein the dental office furniture includes a dental chair and said docking station is configured to be mounted under a delivery unit of said dental chair.

18. The intraoral digital camera system of claim 15, wherein the temperature control circuit includes a thermostatic circuit breaker, the thermostatic circuit breaker being configured to prevent current to the lamp in response to a temperature associated with the light source exceeding a predetermined temperature level.

19. The intraoral digital camera system of claim 15, wherein the switching arrangement is configured to control activation of the lamp and start transmission of video signals from the camera in response to the camera being removed from the holster and the switching arrangement being configured to control deactivation of the lamp and stop transmission of video signals from the camera in response to the camera being placed in the holster.

20. The intraoral digital camera system of claim 15, wherein said power supply is configured to generate 12 VDC and the docking station further includes a 12 VDC input connection.

* * * * *

UNITED STATES PATENT AND TRADEMARK OFFICE
CERTIFICATE OF CORRECTION

PATENT NO. : 7,086,859 B2
APPLICATION NO. : 10/458417
DATED : August 8, 2006
INVENTOR(S) : Gregorio et al.

It is certified that error appears in the above-identified patent and that said Letters Patent is hereby corrected as shown below:

On the Title page, Field 57, ABSTRACT, "The Present invention is a true digital output intraoral camera with a docking station" should be -- The present invention is a true digital output intraoral camera with a compact docking station --, Title page 2, U.S. PATENT DOCUMENTS, "6,230,934 B1, 5/2001, Kramer" should be -- 6,320,934 B1, 11/2001, Carroll et al. --, Title page 2, U.S. PATENT DOCUMENTS, "6,761,561 B1" should be -- 6,761,561 B2 --.

Signed and Sealed this

Twentieth Day of November, 2007

JON W. DUDAS
*Director of the United States Patent and Trademark Office*